US 9,389,190 B2

(12) United States Patent
Tsuyuki

(10) Patent No.: US 9,389,190 B2
(45) Date of Patent: Jul. 12, 2016

(54) X-RAY CT APPARATUS WITH CORRECTION FOR OBJECT SHIFT IN RESPONSE TO MOVEMENT OF THE SCANNING BED

(71) Applicants: Kabushiki Kaisha Toshiba, Minato-ku (JP); Toshiba Medical Systems Corporation, Otawara-shi (JP)

(72) Inventor: Masaharu Tsuyuki, Nasushiobara (JP)

(73) Assignees: KABUSHIKI KAISHA TOSHIBA, Minato-ku (JP); Toshiba Medical Systems Corporation, Otawara-shi (JP)

( * ) Notice: Subject to any disclaimer, the term of this patent is extended or adjusted under 35 U.S.C. 154(b) by 146 days.

(21) Appl. No.: 14/177,824

(22) Filed: Feb. 11, 2014

(65) Prior Publication Data

US 2014/0161222 A1    Jun. 12, 2014

Related U.S. Application Data

(63) Continuation of application No. PCT/JP2013/073849, filed on Sep. 4, 2013.

(30) Foreign Application Priority Data

Sep. 4, 2012   (JP) ................................. 2012-194431
Aug. 29, 2013  (JP) ................................. 2013-178708

(51) Int. Cl.
   *G01N 23/04*   (2006.01)
   *A61B 6/03*    (2006.01)
   *A61B 6/04*    (2006.01)

(52) U.S. Cl.
   CPC ............... *G01N 23/046* (2013.01); *A61B 6/03* (2013.01); *A61B 6/0407* (2013.01); *A61B 6/0457* (2013.01)

(58) Field of Classification Search
   CPC .............................. A61B 6/032; A61B 6/0457
   See application file for complete search history.

(56) References Cited

U.S. PATENT DOCUMENTS 6,185,271 B1 *  2/2001  Kinsinger .............. A61B 6/032
                                              378/19
6,269,501 B1 *  8/2001  Li ........................ A61B 6/0457
                                              378/20

(Continued)

FOREIGN PATENT DOCUMENTS

CN    101455572 A    6/2009
CN    101879069 A    11/2010

(Continued)

OTHER PUBLICATIONS

International Search Report issued Oct. 8, 2013 in PCT/JP2013/073849 (English translation only).

(Continued)

*Primary Examiner* — Robert Kim
*Assistant Examiner* — Sean Luck
(74) *Attorney, Agent, or Firm* — Oblon, McClelland, Maier & Neustadt, L.L.P.

(57) ABSTRACT

An X-ray CT apparatus includes an X-ray tube, X-ray detector detecting the X-rays transmitted through an object, data acquisition unit acquiring projection data of the object based on an output from the X-ray detector, bed driving control unit moving a top to place the object along a long-axis direction of the top, image processing unit generating a reconstructed image based on the projection data, positional shift amount detection unit detecting a shift amount of a relative position between the top and the object, and positional shift processing unit performing processing based on a detection result obtained by the positional shift amount detection unit, in accordance with movement of the top by the bed driving control unit.

21 Claims, 8 Drawing Sheets

(56) References Cited

U.S. PATENT DOCUMENTS

| | | | | |
|---|---|---|---|---|
| 6,324,246 B1* | 11/2001 | Ruimi | A61B 6/032 | 378/15 |
| 6,470,519 B1* | 10/2002 | Pattee | A61B 6/105 | 188/31 |
| 6,526,117 B1* | 2/2003 | Okerlund | A61B 6/032 | 378/4 |
| 7,260,253 B2* | 8/2007 | Rahn | G01N 15/1468 | 378/21 |
| 2004/0042581 A1* | 3/2004 | Okerlund | A61B 5/0456 | 378/4 |
| 2004/0062341 A1* | 4/2004 | Popescu | A61B 6/032 | 378/4 |
| 2005/0074085 A1* | 4/2005 | Hsieh | A61B 5/055 | 378/4 |
| 2007/0076852 A1* | 4/2007 | Ishikawa | A61B 6/0457 | 378/208 |
| 2007/0086577 A1* | 4/2007 | Kobayashi | A61B 6/0457 | 378/195 |
| 2007/0110211 A1* | 5/2007 | Hsieh | A61B 6/032 | 378/16 |
| 2008/0098525 A1* | 5/2008 | Doleschal | A61B 6/0457 | 5/600 |
| 2008/0317203 A1* | 12/2008 | Ferrand | A61B 6/0457 | 378/65 |
| 2009/0080595 A1* | 3/2009 | Nishii | A61B 6/032 | 378/4 |
| 2009/0092224 A1* | 4/2009 | Nishide | A61B 6/032 | 378/13 |
| 2009/0110139 A1* | 4/2009 | Noshi | A61B 6/032 | 378/4 |
| 2010/0037394 A1* | 2/2010 | Hayes | A61B 6/0457 | 5/601 |
| 2010/0208864 A1 | 8/2010 | Soejima | | |
| 2010/0246752 A1* | 9/2010 | Heuscher | A61B 6/06 | 378/4 |
| 2012/0002790 A1* | 1/2012 | Tanaka | A61B 6/025 | 378/198 |
| 2012/0189095 A1* | 7/2012 | Ruijters | A61B 5/06 | 378/19 |

FOREIGN PATENT DOCUMENTS

| | | |
|---|---|---|
| JP | 2-185235 A | 7/1990 |
| JP | 3-70548 A | 3/1991 |
| JP | 6-78916 A | 3/1994 |
| JP | 2002-200069 A | 7/2002 |
| JP | 2006-158690 A | 6/2006 |
| JP | 2006-528892 A | 12/2006 |
| JP | 2010-214091 A | 9/2010 |
| JP | 2011-62445 A | 3/2011 |

OTHER PUBLICATIONS

International Search Report issued on Oct. 8, 2013 for PCT/JP2013/073849 filed on Sep. 4, 2013 with English Translation of Categories.
International Written Opinion mailed on Oct. 8, 2013 for PCT/JP2013/073849 filed on Sep. 4, 2013.
Notice of Allowance mailed on Mar. 24, 2016 in Chinese Application No. 201380001569.3.

* cited by examiner

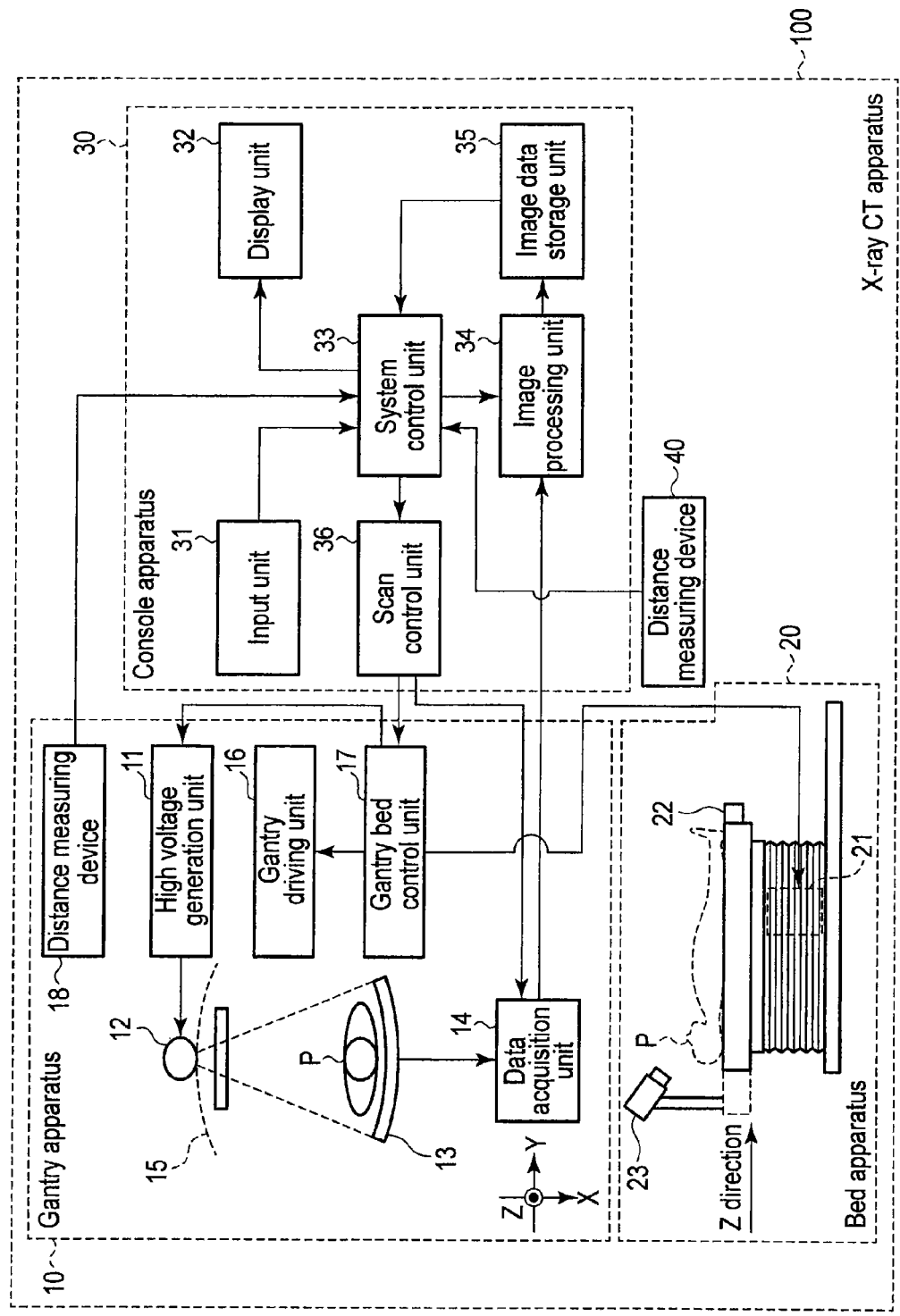
F I G. 1

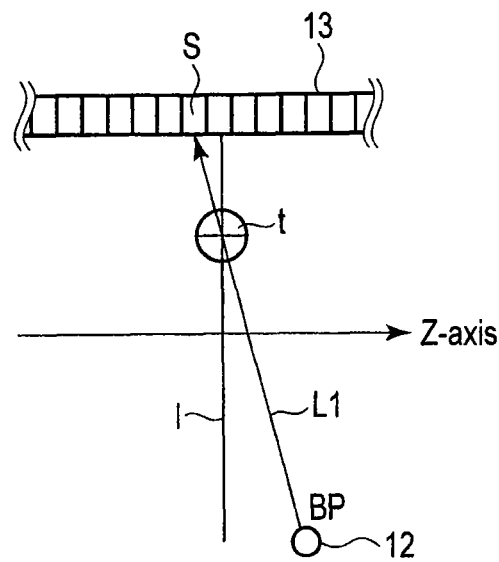
Without movement
F I G. 5
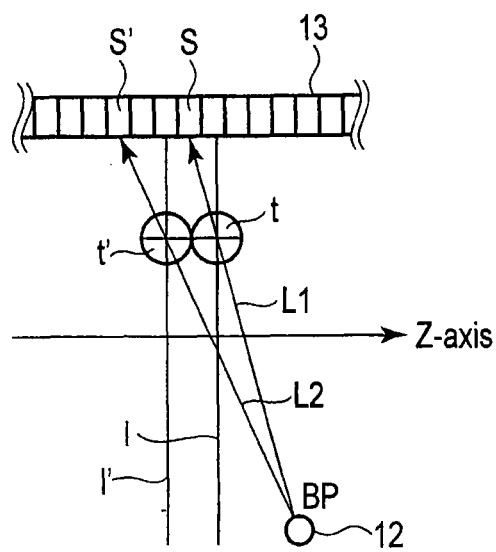
With movement
F I G. 6

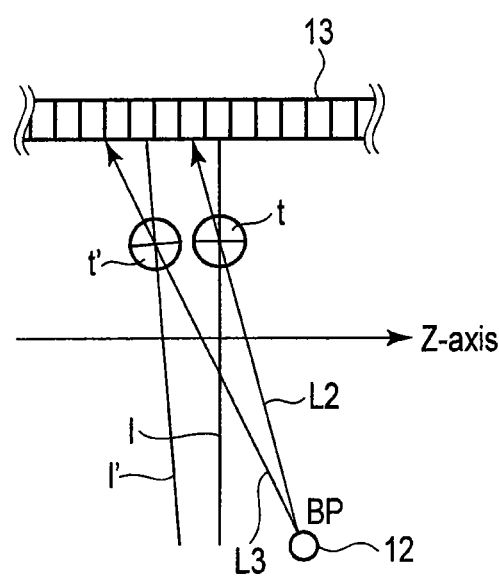
F I G. 7

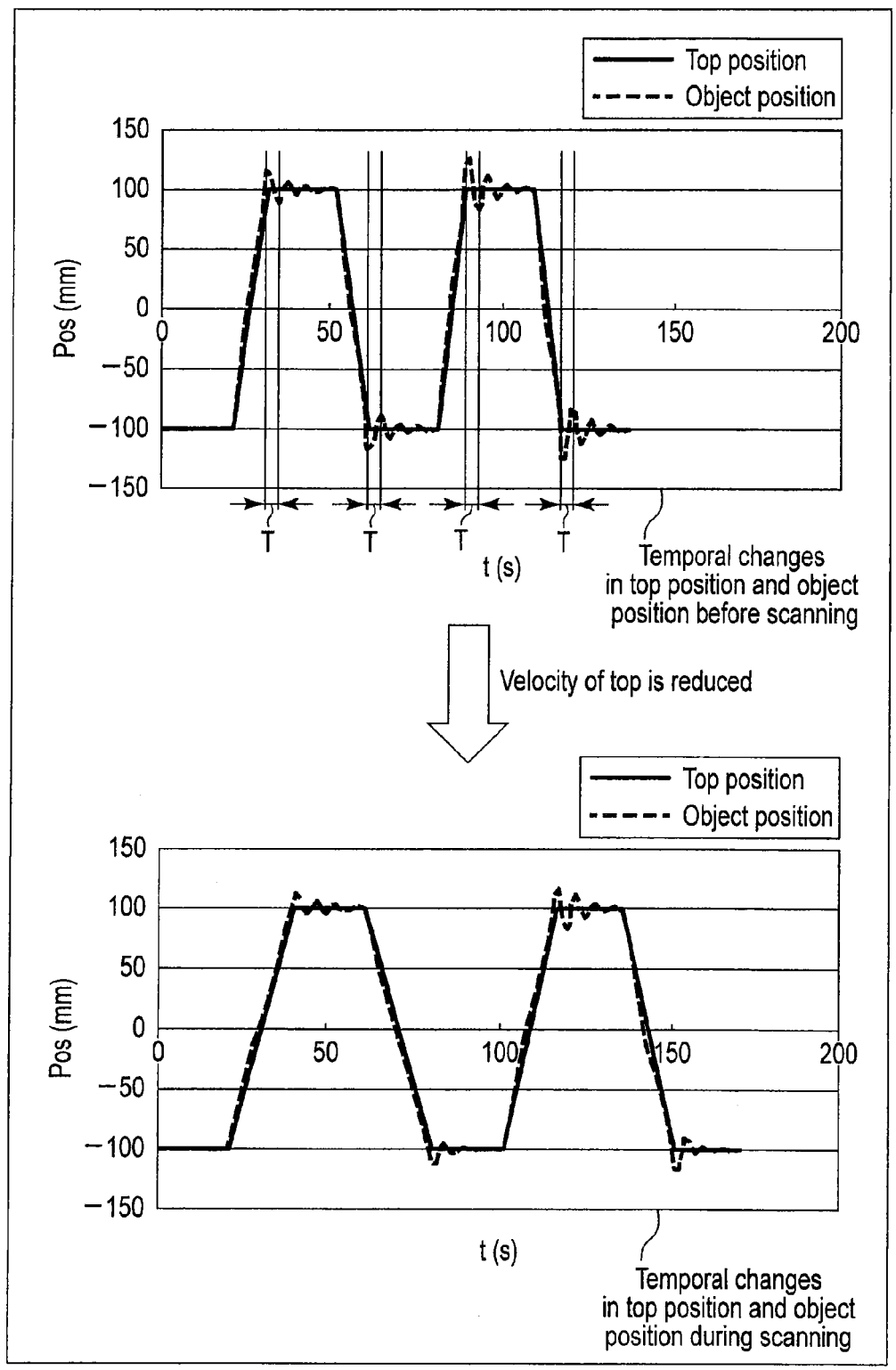
F I G. 8

X-RAY CT APPARATUS WITH CORRECTION FOR OBJECT SHIFT IN RESPONSE TO MOVEMENT OF THE SCANNING BED

CROSS-REFERENCE TO RELATED APPLICATIONS

This application is a Continuation Application of PCT Application No. PCT/JP2013/073849, filed Sep. 4, 2013 and based upon and claims the benefit of priority from the Japanese Patent Application No. 2012-194431, filed Sep. 4, 2012 and the Japanese Patent Application No. 2013-178708, filed Aug. 29, 2013, the entire contents of all of which are incorporated herein by reference.

FIELD

Embodiments described herein relate generally to an X-ray CT apparatus.

BACKGROUND

As imaging techniques using X-ray CT (Computed Tomography) apparatuses, there are known, for example, an imaging technique called "jog shuttle scanning" and an imaging technique called "helical shuttle scanning".

Jog shuttle scanning is configured to sequentially repeat moving and stopping a bed for each slice and execute X-ray imaging at the time of the stoppage of the bed. This can reduce artifacts but prolongs the imaging time.

Helical shuttle scanning is configured to irradiate an object with X-rays in a helical pattern by continuously and reciprocatingly moving a top while continuously rotating an X-ray tube on a circular orbit centered on the object. This can obtain a tomographic image of the object, covering a wide range and having excellent continuity.

In X-ray imaging using jog shuttle scanning and helical shuttle scanning, the bed on which an object is placed is driven to obtain data of a wide region. Along with this movement of the bed, the relative positional relationship between the object placed on the bed and the bed changes. In other words, the position of the object shifts relative to the bed along with the driving of the bed.

In this case, although the X-ray CT apparatus side is grasping the transition of the position of the bed itself, it cannot grasp the transition of the position of the object on the bed (a change in the relative position between the bed and the object). That is, in the reconstruction of projection data, consideration is given to only the transition of the position of the bed itself.

As a consequence, the reconstructed image obtained by reconstructing projection data reflects the positional shift of the object relative to the bed (a change in the relative position between the bed and the object). This may cause, for example, artifacts and the like and degrade the accuracy and reliability of the reconstructed image.

BRIEF DESCRIPTION OF THE DRAWINGS

FIG. 1 is a block diagram showing an example of the arrangement of an X-ray CT apparatus according to an embodiment.

FIG. 5 is a sectional view taken along a plane including straight lines L1 and L2 indicating the paths of X-rays in the schematic view of FIG. 4 according to this embodiment.

FIG. 6 is a sectional view taken along a plane including straight lines L1 and L2 indicating the paths of X-rays in the schematic view of FIG. 4 according to this embodiment.

FIG. 7 is a schematic view showing an example in which the movement of the object on the top is not movement in a direction (Z-axis direction) parallel to the moving direction of the top according to this embodiment.

FIG. 8 is a graph showing temporal changes in the position of the top and the position of the object upon execution of the first reciprocating movement, together with temporal changes in the position of the top and the position of the object upon execution of the second reciprocating movement, according to the second modification of this embodiment.

DETAILED DESCRIPTION

An X-ray CT apparatus according to an embodiment includes an X-ray tube, an X-ray detector, a data acquisition unit, a bed driving control unit, an image processing unit, a positional shift amount detection unit, and a positional shift processing unit.

The X-ray tube generates X-rays.

The X-ray detector is provided to face the X-ray tube and detects the X-rays transmitted through an object.

The data acquisition unit acquires projection data of the object based on an output from the X-ray detector.

The bed driving control unit moves a top to place the object along a long-axis direction of the top.

The image processing unit generates a reconstructed image based on the projection data.

The positional shift amount detection unit detects a shift amount of a relative position between the top and the object.

The positional shift processing unit performs processing based on a detection result obtained by the positional shift amount detection unit, in accordance with movement of the top by the bed driving control unit.

An X-ray CT apparatus according to an embodiment will be described below with reference to the accompanying drawings.

Figure 2:
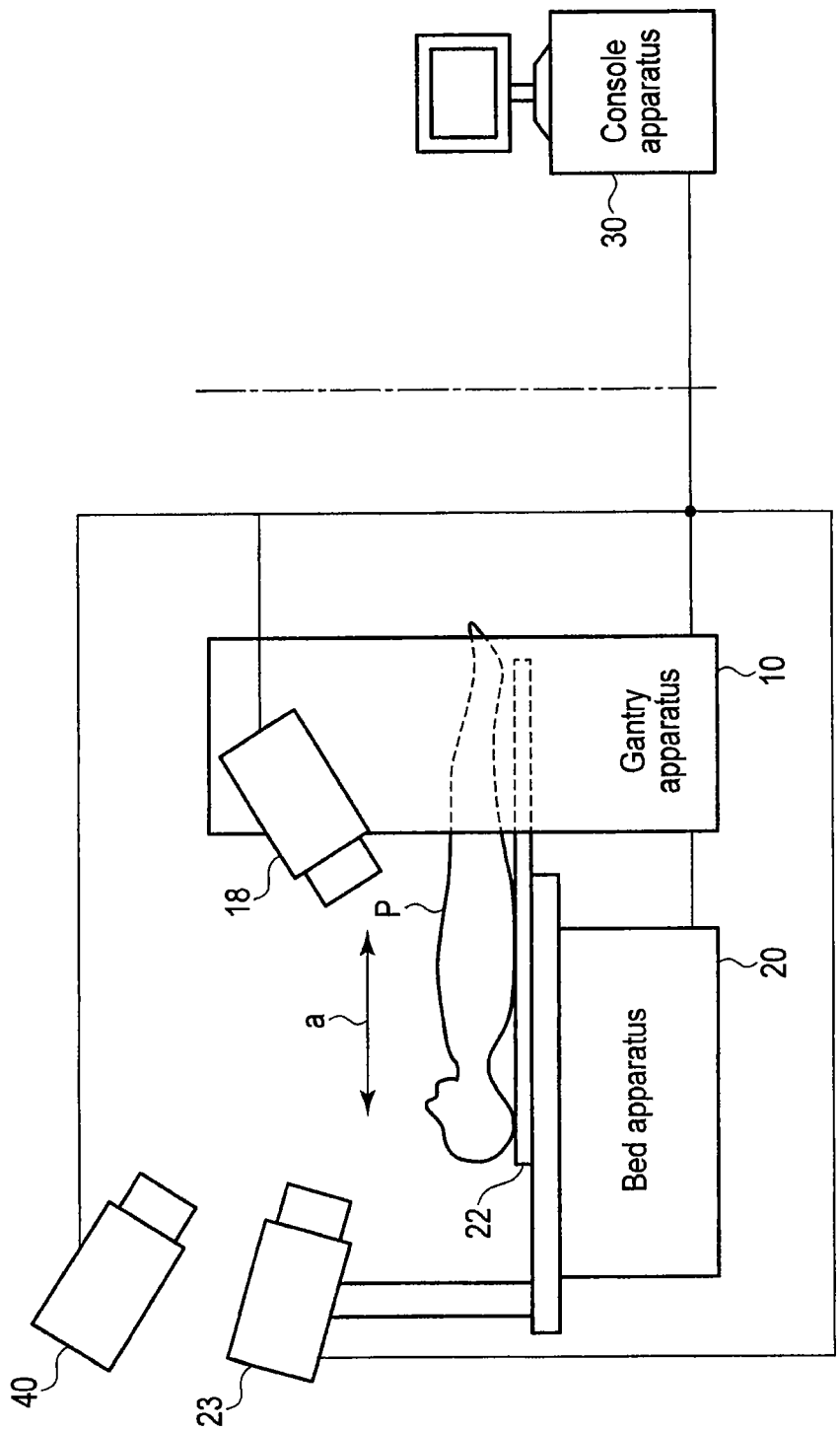
FIG. 2 is a schematic view showing the overall X-ray CT apparatus according to this embodiment.

FIG. 1 is a block diagram showing an example of the arrangement of the X-ray CT apparatus according to this embodiment. FIG. 2 is a schematic view showing an overall X-ray CT apparatus 100 according to the embodiment.

As shown in FIG. 1, the X-ray CT apparatus 100 according to this embodiment includes a gantry apparatus 10, a bed apparatus 20, a console apparatus 30, and a distance measuring device 40.

The gantry apparatus 10 is an apparatus which irradiates an object P with X-rays, detects the X-rays transmitted through the object P, and outputs the resultant data to the console apparatus 30. More specifically, the gantry apparatus 10 includes a high voltage generation unit 11, an X-ray tube 12, an X-ray detector 13, a data acquisition unit 14, a rotating frame 15, a gantry driving unit 16, a gantry bed control unit 17, and a distance measuring device 18.

The high voltage generation unit 11 applies a high voltage to the X-ray tube 12 under the control of the gantry bed control unit 17.

The X-ray tube 12 is a vacuum tube which generates X-rays upon reception of the high voltage applied from the high voltage generation unit 11. The X-ray tube 12 is an X-ray source which irradiates the object P with X-rays.

The X-ray detector 13 detects the X-rays transmitted through the object P. The data acquisition unit 14 generates projection data (X-ray image data) by using the X-rays detected by the X-ray detector 13.

The rotating frame 15 is an annular frame. The rotating frame 15 supports the X-ray tube 12 and the X-ray detector 13 such that they face each other through the object P.

The gantry driving unit 16 drives the gantry under the control of the gantry bed control unit 17. More specifically, the gantry driving unit 16 continuously rotates the X-ray tube 12 and the X-ray detector 13 on a circular orbit centered on the object P by continuously rotating the rotating frame 15 by driving a motor.

The gantry bed control unit 17 controls the high voltage generation unit 11, the gantry driving unit 16, and a bed driving unit 21 under the control of a scan control unit 36 (to be described later). The gantry bed control unit 17 decides, in advance, the rotational angle of the X-ray tube 12 at the time of the start of irradiation in a forward scan and the rotational angle of the X-ray tube 12 at the time of the start of a backward scan.

The distance measuring device 18 measures the movement (position) of the object P placed on a top 22 of the bed apparatus 20. The distance measuring device 18 outputs the measurement result to a system control unit 33 of the console apparatus 30. The system control unit 33 calculates the shift amount of the relative position between the top 22 and the object P based on the measurement result obtained by the distance measuring device 18. The distance measuring device 18 is, in particular, an image sensor such as a camera, an optical distance meter using, for example, infrared light, laser light, or stereoscopy, acoustic distance meter, or the like.

That is, the distance measuring device 18 and the system control unit 33 function as a positional shift amount detection unit which detects the shift amount of the relative position between the top 22 and the object P. The system control unit 33 functions as a positional shift processing unit which performs processing based on the relative positional shift amount detected by the distance measuring device 18.

Note that the X-ray CT apparatus 100 according to this embodiment includes, as distance measuring devices, a distance measuring device 23 provided on the bed apparatus 20 and the distance measuring device 40 provided independently of the gantry apparatus 10 and the bed apparatus 20, in addition to the distance measuring device 18 or the like provided on the gantry apparatus 10. However, it suffices if the apparatus includes at least one of distance measuring devices.

Obviously, the gantry bed control unit 17 (system control unit 33) which controls the bed driving unit 21 has the movement (position) information of the top 22 itself of the bed apparatus 20. Note that the distance measuring devices 18, 23, and 40 may measure the movement (position) of the top 22 at the time of measurement of the movement (position) of the object P.

The bed apparatus 20 is a table on which the object P to be imaged is placed. The bed apparatus 20 includes the bed driving unit 21, the top 22, and the distance measuring device 23. The bed driving unit 21 continuously and reciprocatingly moves the top 22 in the body axis direction of the object P (the direction indicated by the arrow indicating the Z direction in FIG. 1 and the long-axis direction of the top) by driving the motor under the control of the gantry bed control unit 17. The top 22 is a plate on which the object P is placed.

The distance measuring device 23 measures the movement of the object P placed on the top 22 of the bed apparatus 20 as in the distance measuring device 18. The distance measuring device 23 outputs the measurement result to the system control unit 33 of the console apparatus 30. The distance measuring device 23 is, in particular, an image sensor such as a camera, an optical distance meter using, for example, infrared light, laser light, or stereoscopy, an acoustic distance meter, or the like. In addition, the distance measuring device 23 may be configured such that a mat member (not shown) incorporating, for example, a strain sensor is arranged on the top 22, and the object P is placed on the mat member.

The console apparatus 30 accepts the operation of the X-ray CT apparatus 100 by the operator and generates a reconstructed image from the projection data acquired by the gantry apparatus 10 by executing reconstruction processing using, for example, a back projection scheme based on back projection computation. More specifically, the console apparatus 30 includes an input unit 31, a display unit 32, the system control unit 33, an image processing unit 34, an image data storage unit 35, and a scan control unit 36.

The input unit 31 includes a mouse and a keyboard. The input unit 31 is used to input an instruction to the X-ray CT apparatus 100. For example, the input unit 31 accepts scan condition settings.

The display unit 32 is a display such as an LCD (Liquid Crystal Display), which displays various types of information. For example, the display unit 32 displays the images stored in an image data storage unit 35 and a GUI (Graphical User Interface) for accepting various types of instructions from the operator.

The system control unit 33 is an integrated circuit such as an ASIC (Application Specific Integrated Circuit) or FPGA (Field Programmable Gate Array) or an electronic circuit such as a CPU (Central Processing Unit) or MPU (Micro Processing Unit). More specifically, the system control unit 33 controls the overall X-ray CT apparatus 100 by controlling the gantry apparatus 10, the bed apparatus 20, and the console apparatus 30. For example, the system control unit 33 controls the scan control unit 36 to acquire projection data. In addition, for example, the system control unit 33 controls the image processing unit 34 to reconstruct an image from projection data.

In addition, the system control unit 33 calculates the shift amount of the relative position between the top 22 and the object P by using the measurement results obtained by the distance measuring devices 18, 23, and 40. That is, the system control unit 33 functions as a positional shift amount detection unit which calculates the shift amount of the relative position, together with the distance measuring devices 18, 23, and 40.

The system control unit 33 performs processing for suppressing/informing a reconstructed image deterioration caused by the shift of the relative position by using the shift amount of the relative position. As described above, the system control unit 33 functions as a positional shift processing unit which performs processing based on the shift amount of the relative position. Note that the details of processing will be described later by citing concrete examples.

The image processing unit 34 is an integrated circuit such as an ASIC or FPGA or an electronic circuit such as a CPU or MPU. The image processing unit 34 performs various types of processing for the projection data generated by the data acquisition unit 14. More specifically, the image processing unit 34 performs preprocessing such as sensitivity correction for the projection data generated by the data acquisition unit 14. The image processing unit 34 performs reconstruction processing for the image based on the reconstruction conditions instructed from the system control unit 33. The image processing unit 34 stores the generated reconstructed image in the image data storage unit 35. The image processing unit 34 performs this reconstruction processing by, for example, the back projection scheme based on back projection computation.

The image data storage unit 35 is a semiconductor memory device such as a RAM (Random Access Memory), a ROM (Read Only Memory), or a flash memory, a hard disk, an optical disk, or the like. The image data storage unit 35 stores the image reconstructed by the image processing unit 34. The scan control unit 36 is an integrated circuit such as an ASIC or FPGA or an electronic circuit such as a CPU or MPU. The scan control unit 36 controls the gantry bed control unit 17 based on the scan conditions instructed from the system control unit 33.

The distance measuring device 40 measures the movement of the object P placed on the top 22 of the bed apparatus 20 as with the distance measuring devices 18 and 23. The distance measuring device 40 outputs the measurement result to the system control unit 33 of the console apparatus 30. The distance measuring device 40 is, in particular, an image sensor such as a camera, an optical distance meter using, for example, infrared light, laser light, or stereoscopy, an acoustic distance meter, or the like. In this case, for example, the distance measuring device 40 is installed on a wall of an examination room.

The gantry apparatus 10, the bed apparatus 20, and the console apparatus 30 are installed, as exemplified by FIG. 2. The broken line shown in FIG. 2 indicates the boundary between a scanner room in which the gantry apparatus 10 and the bed apparatus 20 are installed and a console room in which the console apparatus 30 is installed.

The arrow denoted by reference symbol a shown in FIG. 2 indicates the body axis direction of the object P (or the long-axis direction of the top 22). In this case, the top 22 continuously and reciprocatingly moves in the first direction (e.g., the forward direction) parallel to the body axis direction (or the long-axis direction of the top 22) of the object P and the second direction (e.g., the backward direction) opposite to the first direction.

The X-ray CT apparatus 100 according to this embodiment is configured to include at least one of the distance measuring devices 18, 23, and 40 as described above to measure the movement (detect the position) of the object P caused by the movement or the like of the top 22 and calculate the shift amount of the relative position between the object P and the top 22 based on the measured movement.

Figure 3:
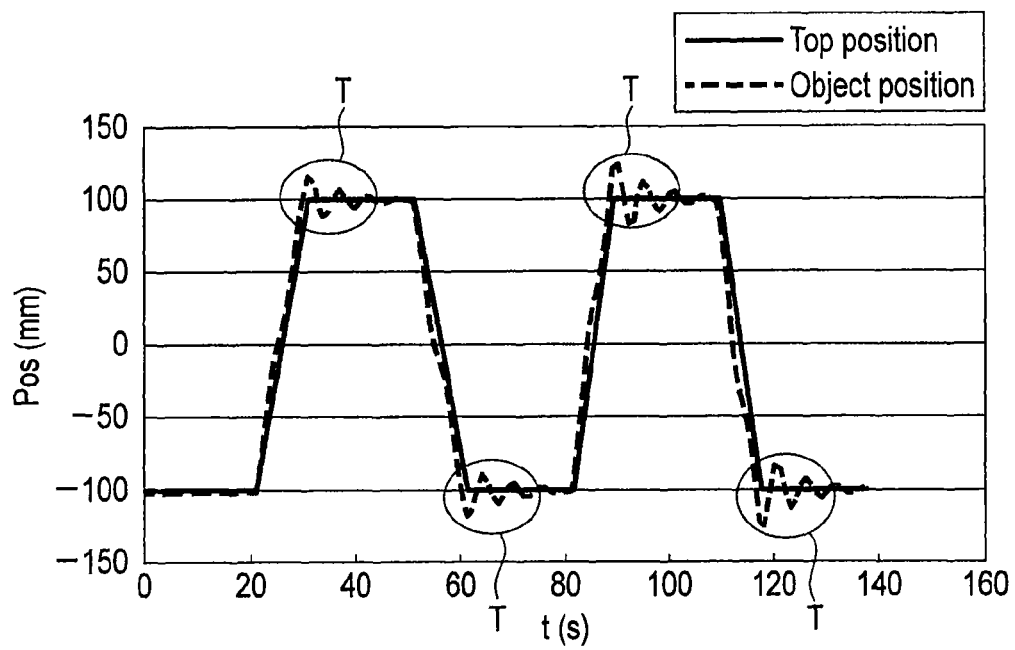
FIG. 3 is a graph showing an example of temporal changes in the position of the top and the position of an object when the top continuously and reciprocatingly moves in the body axis direction of the object according to this embodiment.

FIG. 3 is a graph showing an example of temporal changes in the position of the top 22 and the position of the object P when the bed driving unit 21 continuously and reciprocatingly moves the top 22 in the body axis direction of the object under the control of the system control unit 33 (gantry bed control unit 17).

Processing using the measurement results obtained by the distance measuring devices 18, 23, and 40 will be described in detail below with reference to FIG. 3. Referring to FIG. 3, the solid line indicates a graph representing a temporal change in the position of the top 22, and the broken line indicates a graph representing a temporal change in the position of the object P.

As shown in FIG. 3, the object P does not perfectly follow the movement of the top 22. The object P slightly vibrates even after the top 22 stops moving and becomes at rest. For this reason, the relative position with respect to the top 22 shifts.

Figure 4:
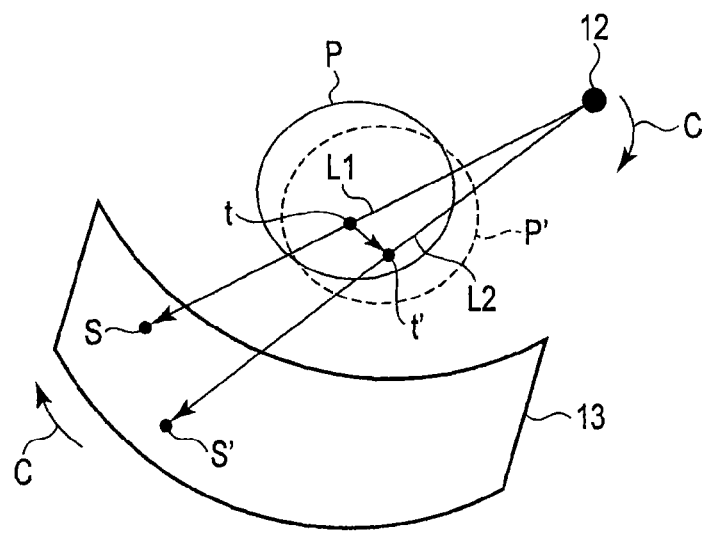
FIG. 4 is a schematic view showing how the position of an X-ray transmitted through each point in an object which strikes an X-ray detector shifts from the original position due to a shift of the relative position between the top and the object according to this embodiment.

FIG. 4 is a schematic view showing how the position of an X-ray transmitted through each point in the object P which strikes the X-ray detector 13 shifts from the original position due to a shift of the relative position between the top 22 and the object P.

FIGS. 5 and 6 are sectional views respectively taken along straight lines L1 and L2 indicating the paths of X-rays in the schematic view of FIG. 4.

In the case shown in FIGS. 4, 5, and 6, when the position of the object P shifts to the position of an object P' indicated by the broken line, the position of a point t in the object P moves to a point t'. In this case, a straight line 1 shown in each of FIGS. 5 and 6 is a straight line indicating the position of a plane in the Z-axis direction for which the image processing unit 34 performs back projection computation. As shown in FIG. 6, a region in the object P which should be located at the position of the plane (on the straight line 1) for which back projection computation is performed shifts to the position indicated by a straight line 1' in FIG. 6.

As a result, a position (a channel and a segment) s on the X-ray detector 13 associated with imaging of the point t in the object P shifts to a position s'. That is, in the case shown in FIGS. 4 and 6, the path along which an X-ray emitted by the X-ray tube 12 is transmitted through the point t and strikes the X-ray detector 13 shifts from the straight line L1 to the straight line L2.

The X-ray CT apparatus according to this embodiment has been made in consideration of such situations, and the system control unit 33 calculates the shift amount of the relative position between the top 22 and the object P based on the measurement performed by the distance measuring devices 18, 23, and 40, and suppresses/informs a reconstructed image deterioration caused by the shift of the relative position. This processing will be described in detail below by citing concrete examples.

Processing Example 1

In processing example 1, when driving the top 22 (i.e., in accordance with the movement of the top 22) via the gantry bed control unit 17 and the bed driving unit 21, the system control unit 33 calculates the shift amount of the relative position (to be abbreviated as the "positional shift amount" hereinafter) between the top 22 and the object P and then compares the positional shift amount with a predetermined threshold. For example, the system control unit 33 notifies the operator of the X-ray CT apparatus 100 of this comparison result by causing the display unit 32 to display it.

With this operation, the operator of the X-ray CT apparatus 100 can recognize that there is a possibility that the reconstructed image generated by the image processing unit 34 of the console apparatus 30 (or generated by X-ray imaging based on similar conditions (the moving velocity and acceleration of the top 22)) include artifacts and the like (can recognize that the accuracy (reliability) of a reconstructed image is not high).

In the case shown in FIG. 3, the period denoted by reference symbol T is a period during which the positional shift amount exceeds the predetermined threshold.

Note that only when the positional shift amount exceeds the predetermined threshold, the X-ray CT apparatus 100 may notify the operator of the corresponding information.

Processing 2

In processing example 2, when driving the top 22 via the gantry bed control unit 17 and the bed driving unit 21, the system control unit 33 calculates the positional shift amount between the top 22 and the object P, and then compares the positional shift amount with a predetermined threshold. Subsequently, the system control unit 33 determines whether the positional shift amount exceeds the predetermined threshold. Upon determining that the positional shift amount exceeds the predetermined threshold, the system control unit 33 controls the bed driving unit 21 via the gantry bed control unit 17 to reduce at least one of the moving velocity and acceleration of the top 22 when driving the top 22 next.

Pluralities of moving velocities and accelerations are set stepwise for the top 22 and recorded on a nonvolatile memory (not shown) or the like provided in the system control unit 33. In other words, a plurality of driving modes like that indicated by the graph associated with the top 22 which is shown in FIG. 3 are set and recorded on a nonvolatile memory (not shown) or the like provided in the system control unit 33.

The system control unit 33 may reduce at least one of the moving velocity and acceleration of the top 22 stepwise sequentially based on a driving mode recorded on the nonvolatile memory (not shown) or the like. This makes it possible to move the top 22 at the highest velocity within the range in which no adverse effect is imposed on a reconstructed image, and hence it is possible to obtain a reconstructed image with high accuracy (reliability) by shortening sampling intervals as much as possible.

This makes it possible to suppress the relative positional shift between the top 22 and the object P and obtain a reconstructed image with high accuracy (reliability).

Processing 3

In processing 3, when driving the top 22 via the gantry bed control unit 17 and the bed driving unit 21, the system control unit 33 calculates the positional shift amount between the top 22 and the object P and then compares the positional shift amount with a predetermined threshold. The system control unit 33 then determines whether the positional shift amount exceeds the predetermined threshold. Upon determining that the positional shift amount exceeds the predetermined threshold, the system control unit 33 notifies the operator of the X-ray CT apparatus 100, via the gantry bed control unit 17, of a recommendation to reduce at least one of the moving velocity and acceleration of the top 22 when driving the top 22 next.

More specifically, the system control unit 33 notifies the operator of the X-ray CT apparatus 100 of a recommendation to reduce at least one of the moving velocity and acceleration of the top 22 when driving the top 22 next by, for example, displaying the corresponding information on the display unit 32.

The operator may use, for example, the input unit 31 to reduce at least one of the moving velocity and acceleration of the top 22 stepwise sequentially by referring to a driving mode recorded on the nonvolatile memory (not shown) or the like.

This makes it possible to suppress the relative positional shift between the top 22 and the object P and obtain a reconstructed image with high accuracy (reliability).

Processing 4

In processing 4, when driving the top 22 via the gantry bed control unit 17 and the bed driving unit 21, the system control unit 33 determines whether the positional shift amount exceeds the predetermined threshold. Upon determining that the positional shift amount exceeds the predetermined threshold, the system control unit 33 controls the high voltage generation unit 11 via the scan control unit 36 and the gantry bed control unit 17 to delay the irradiation timing of X-rays by the X-ray tube 12 and make it execute X-ray irradiation after the object P stops vibrating.

More specifically, for example, upon detecting that the positional shift amount becomes less than the predetermined threshold, the system control unit 33 controls the X-ray tube 12 to execute X-ray irradiation.

Processing 5

In processing 5, when driving the top 22 via the gantry bed control unit 17 an the bed driving unit 21, the system control unit 33 controls the image processing unit 34 to perform reconstruction computation by selecting projection data used for reconstruction computation (selecting a channel and a segment in the X-ray detector 13) so as to cancel the relative positional shift between the top 22 and the object P in the reconstruction computation by the image processing unit 34.

More specifically, when the position of the object P shifts to the position of the object P' indicated by the broken line as indicated by the case shown in FIGS. 4 and 6 described above, a region in the object P which should be located at a position (on the straight line 1) on a plane for which back projection computation is performed as shown in FIG. 6 shifts to the position indicated by the straight line 1'.

As a result, the position (channel and segment) s on the X-ray detector 13 associated with imaging of the point t of the object P shifts to the position s'. When, therefore, performing back projection computation at the position of the point t of the object P, the system control unit 33 uses the data of the path indicated by the straight line L2.

That is, the system control unit 33 controls the image processing unit 34 so as to use projection data corresponding to the position s' on the X-ray detector 13 for reconstruction computation (so as to select the channel and segment corresponding to the positions') in imaging of the point t in the object P.

In other words, the system control unit 33 controls the image processing unit 34 so as to use the projection data of the path based on consideration given to the relative positional shift amount when performing reconstruction computation for each point in the object. For example, the system control unit 33 estimates the positional shift amount (the movement amount of the object P) for each view and controls the image processing unit 34 to perform reconstruction computation based on the estimation result.

As described above, it is possible to obtain a reconstructed image with high accuracy (high reliability) by performing control to perform reconstruction computation by selecting a channel and a segment on the X-ray detector 13 in accordance with the positional shift amount so as to cancel the relative positional shift with respect to each point, of the object P, for which reconstruction computation is performed.

Note that the X-ray CT apparatus according to this embodiment can be applied to even a case in which the movement of the object P on the top 22 is not movement in a direction (Z-axis direction) parallel to the moving direction of the top 22. This case will be described in detail below.

FIG. 7 is a schematic view showing an example of a case in which the movement of the object P on the top 22 is not movement in a direction (Z-axis direction) parallel to the moving direction of the top 22. In the case shown in FIG. 7, a region in the object P which should be located at the original position (on the straight line 1) on a plane for which back projection computation is performed has shifted to the position indicated by the straight line 1' without translating relative to the Z-axis (moving with an inclination relative to the Z-axis). Even in such a case, it is possible to perform processing using the data of a path based on consideration given to the relative position when performing back projection computation in the same manner as described above by estimating the movement of each point by using a conventional technique such as performing distance measurement at multiple points and using an analysis model.

As described above, this embodiment can provide an X-ray CT apparatus which can obtain a reconstructed image with high accuracy and reliability by suppressing the influence of the movement (vibration) of an object caused by the movement or the like of the top 22 on which the object is placed.

More specifically, the X-ray CT apparatus according to this embodiment generates a reconstructed image with improved image quality and analysis accuracy mainly by avoiding X-ray imaging in a state in which at least one of the movement and vibration of a patient on the top 22 of the bed apparatus 20 is large and reducing the influence of at least one of the movement and vibration of the patient on the top 22 of the bed apparatus 20 on the reconstructed image.

Note that in the above case, the apparatus performs control based on the "shift amount of the relative position between the top 22 and the object P". However, for example, an acceleration sensor may be attached to the object P, and the apparatus may perform control like that described above based on the "output value from the acceleration sensor".

First Modification

Accumulating data obtained at the time of actual operation of the X-ray CT apparatus according to this embodiment can estimate the time required to stop the movement (vibration) of the object P, which is caused when the top 22 is driven, in accordance with various types of conditions of the object P (e.g., the body type and clothes).

Enabling this estimation allows the system control unit 33 to perform the following operation without performing measurement by a distance measuring device like that described above. Upon estimating that the positional shift amount exceeds the predetermined threshold, the system control unit 33 may execute X-ray irradiation after the movement (vibration) of the object P stops upon delaying the irradiation timing of X-rays by the X-ray tube 12 by controlling the high voltage generation unit 11 based on the estimation result.

This arrangement can further simplify the arrangement of the X-ray CT apparatus 100.

Second Modification

The gantry bed control unit 17 controls the bed driving unit 21 to execute the first reciprocating movement to reciprocatingly move the top 22, on which the object P is placed, along the long-axis direction of the top 22 before scanning the object P.

The distance measuring device 23 and the system control unit 33 function as a positional shift amount detection unit which detects the shift amount of the relative position between the top 22 and the object P. The positional shift amount detection unit detects the shift amount of the relative position between the top 22 and the object P in the first reciprocating movement.

The system control unit 33 functions as a positional shift processing unit which performs processing based on the shift amount of the relative position detected by the distance measuring device 23. The positional shift processing unit determines whether the shift amount of the relative position exceeds a predetermined threshold. If the shift amount of the relative position exceeds the predetermined threshold, the system control unit 33 reduces at least one of the velocity and acceleration of the top 22 in the first reciprocating movement and executes the second reciprocating movement to reciprocatingly move the top 22, together with scanning on the object P. Note that the velocity and acceleration of the top 22 in the second reciprocating movement may be input via the input unit 31.

The shift amount of the relative position oscillates while attenuating along the body axis direction of the object P in the reciprocating movement of the top 22 over a predetermined period from the time of the stoppage of the movement. For example, a predetermined threshold is set in advance with respect to the amplitude value of the oscillation of a shift amount and stored in a storage unit (not shown). A predetermined threshold may be decided based on, for example, a predetermined ratio with respect to a slice thickness. For example, the system control unit 33 may decide a predetermined threshold based on the imaging conditions, slice thickness, diagnosis target region, and the like input via the input unit 31. If, for example, the diagnosis target region is a blood vessel, the slice thickness is set to a small value. This sets the predetermined threshold to a smaller value. If the diagnosis target region is an organ, since the slice thickness is set to a large value, the predetermined threshold becomes large.

In addition, the apparatus may execute the second reciprocating movement before scanning. In this case, the positional shift processing unit may determine again whether the shift amount detected by the second reciprocating movement exceeds a predetermined threshold. That is, the operator can possibly check whether the shift amount of the relative position is equal to or less than the predetermined threshold, by executing the second reciprocating movement before scanning. It is possible to reduce the velocity and acceleration of the top 22 again upon checking this.

FIG. 8 is a graph showing temporal changes in the position of the top and the position of the object upon execution of the first reciprocating movement, together with temporal changes in the position of the top and the position of the object upon execution of the second reciprocating movement. Referring to FIG. 8, each graph indicated by a solid line represents a temporal change in the position of the top 22, and each graph indicated by a broken line represents a temporal change in the position of the object P.

Referring to FIG. 8, the graphs (to be referred to as the first reciprocating movement graphs hereinafter) representing temporal changes in top position and object position before scanning are obtained by executing the first reciprocating movement. As indicated by the first reciprocating movement graphs, in general, the object P does not perfectly follow the movement of the top 22 and slightly vibrates even after the top 22 stops moving and becomes at rest, thereby causing a shift of the relative position with respect to the top 22. Referring to FIG. 8, the period denoted by reference symbol T is a period during which the positional shift amount exceeds the predetermined threshold.

Referring to FIG. 8, the graphs (to be referred to as the second reciprocating movement graphs hereinafter) representing temporal changes in top position and object position during scanning are those obtained by reducing the velocity of the top 22 in the first reciprocating movement. As shown in FIG. 8, the shift amount of the relative position indicated by the second reciprocating movement graphs is smaller than the shift amount of the reciprocating movement indicated by the first reciprocating movement graphs. According to this modification, executing the second reciprocating movement together with scanning can suppress the influence of the movement (vibration) of the object caused by the movement or the like of the top 22 on which the object P is placed, and obtain a reconstructed image with high accuracy and reliability.

Third Modification

The gantry bed control unit 17 controls the bed driving unit 21 to execute the first reciprocating movement to reciprocatingly move the top 22, on which the object P is placed, along the long-axis direction of the top 22 before scanning the object P.

The distance measuring device 23 and the system control unit 33 function as a positional shift amount detection unit which detects the shift amount of the relative position between the top 22 and the object P. The positional shift amount detection unit detects the shift amount of the relative position between the top 22 and the object P in the first reciprocating movement.

The system control unit 33 functions as a positional shift processing unit which performs processing based on the shift amount of the relative position detected by the distance measuring device 23. The positional shift processing unit determines whether the shift amount of the relative position exceeds a predetermined threshold. The system control unit 33 specifies a period during which the shift amount of the relative position is equal to or less than the predetermined threshold, based on a temporal change in the shift amount of the relative position in the first reciprocating movement. The system control unit 33 prolongs a stoppage period during which the top 22 stops in the first reciprocating movement to the specified period. Note that the operator may input a prolonged period of the stoppage period in the second reciprocating movement via the input unit 31.

If the shift amount of the relative position exceeds the predetermined threshold, the system control unit 33 executes the second reciprocating movement to reciprocatingly move the top 22 upon prolonging the stoppage period of the top 22 in the first reciprocating movement. The system control unit 33 executes scanning on the object P in a period during which the shift amount is equal to or less than the predetermined threshold in the second reciprocating movement.

The system control unit 33 may decide an emission stoppage period during which X-ray emission is stopped in the second reciprocating movement, based on a slice thickness and the amplitude value of a shift amount. For example, the system control unit 33 decides a period during which the amplitude value of the shift amount exceeds a predetermined ratio of a slice thickness as an emission stoppage period. The predetermined ratio is, for example, 10%.

Figure 9:
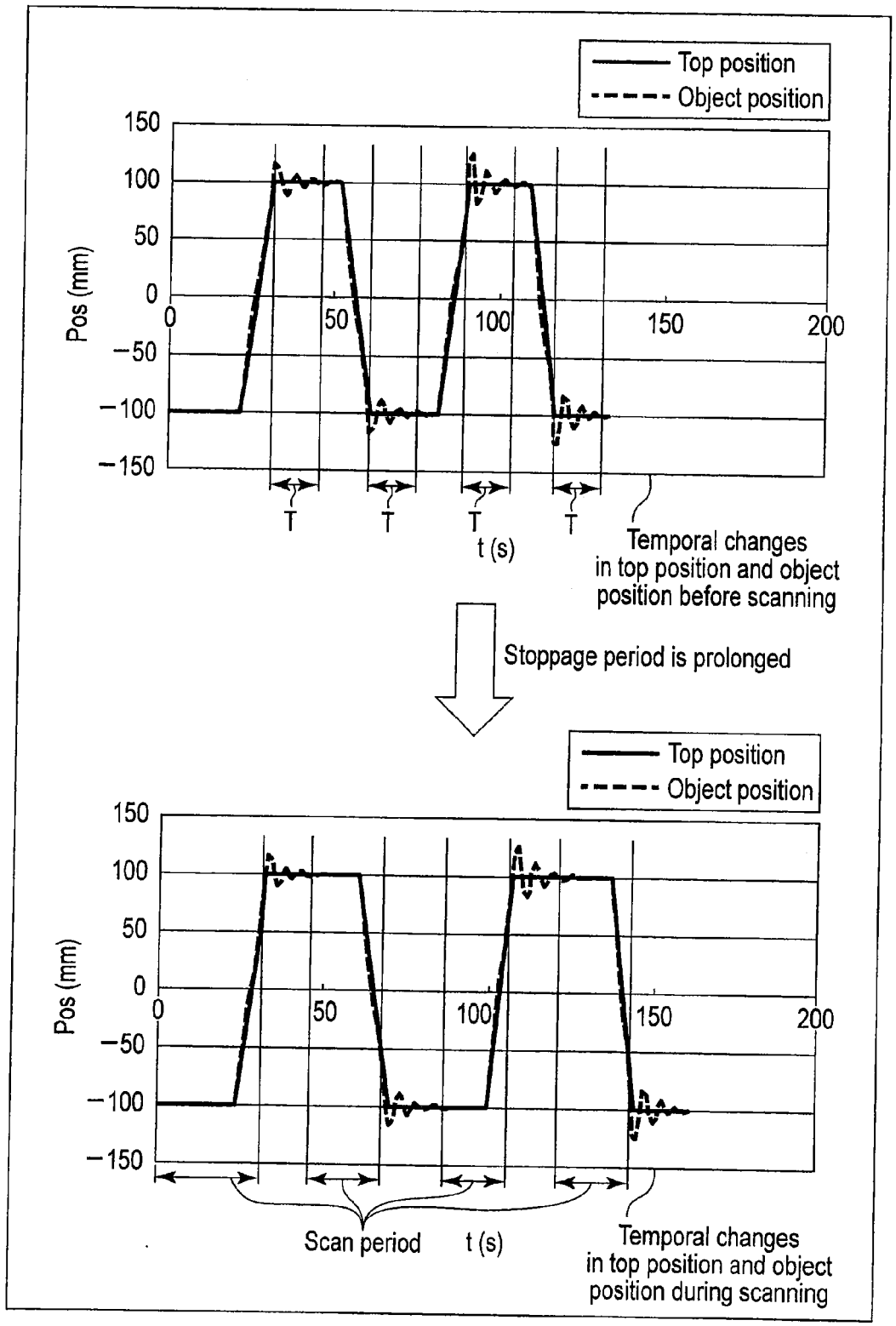
FIG. 9 is a graph showing temporal changes in the position of the top and the position of the object upon execution of the first reciprocating movement, together with temporal changes in the position of the top and the position of the object upon execution of the second reciprocating movement, according to the third modification of this embodiment.

FIG. 9 is a graph showing temporal changes in the position of the top and the position of the object upon execution of the first reciprocating movement, together with temporal changes in the position of the top and the position of the object upon execution of the second reciprocating movement. Referring to FIG. 9, the solid line indicates a graph representing a temporal change in the position of the top 22, and the broken line indicates a graph representing a temporal change in the position of the object P.

Referring to FIG. 9, the graphs (to be referred to as the first reciprocating movement graphs hereinafter) representing temporal changes in top position and object position before scanning are obtained by executing the first reciprocating movement. Referring to FIG. 9, the period denoted by reference symbol T is a period during which the positional shift amount exceeds the predetermined threshold.

Referring to FIG. 9, the graphs (to be referred to as the second reciprocating movement graphs hereinafter) representing temporal changes in top position and object position during scanning are those obtained by prolonging the stoppage period of the top 22 in the first reciprocating movement. As shown in FIG. 9, according to the second reciprocating movement graphs, the apparatus executes scanning on the object P in a plurality of periods during which the shift amount is equal to or less than the predetermined threshold. According to this modification, it is possible to obtain a reconstructed image with high accuracy and reliability by suppressing the movement (vibration) of the object which is caused by the movement or the like of the top 22 on which the object P is placed, by executing scanning in a plurality of periods during which the shift amount is equal to or less than the predetermined threshold, in the second reciprocating movement.

Fourth Modification

The gantry bed control unit 17 controls the bed driving unit 21 to execute the first reciprocating movement to reciprocatingly move the top 22, on which the object P is placed, along the long-axis direction of the top 22 before scanning on the object P.

The distance measuring device 23 and the system control unit 33 function as a positional shift amount detection unit which detects the shift amount of the relative position between the top 22 and the object P. The positional shift amount detection unit detects the shift amount of the relative position between the top 22 and the object P in the first reciprocating movement.

The system control unit 33 functions as a positional shift processing unit which performs processing based on the shift amount of the relative position detected by the distance measuring device 23. The positional shift processing unit determines whether the shift amount of the relative position exceeds a predetermined threshold. More specifically, the positional shift processing unit determines whether the shift amount of the relative position exceeds the predetermined threshold in the stoppage period of the top 22 after the movement of the top 22 in at least one of the forward and backward paths in the first reciprocating movement.

For the sake of simplicity, assume that in the following description, a stoppage period during which the shift amount of the relative position exceeds the predetermined threshold is a period (to be referred to as a post-forward-movement stoppage period hereinafter) after the movement of the top 22 in the forward path in the first reciprocating movement. Note that a stoppage period during which the shift amount of the relative position exceeds the predetermined threshold may be a period after the movement of the top 22 in a backward path in the first reciprocating movement. The reason why a stoppage period during which the shift amount of the relative position exceeds the predetermined threshold occurs after movement in one of forward and backward paths is that the load distribution on the top 22 based on the object P is asymmetric along the long-axis direction of the top 22 (the body axis direction of the object P).

More specifically, the system control unit 33 prolongs the post-forward-movement stoppage period if the shift amount of the relative position exceeds the predetermined threshold in a stoppage period of the top 22 after the movement of the top 22 in the forward path in the first reciprocating movement. Note that the system control unit 33 may reduce at least one of the velocity and acceleration of the top 22 in the forward path in the first reciprocating movement. The system control unit 33 specifies a period during which the shift amount of the relative position is equal to or less than the predetermined threshold, based on a temporal change in the shift amount of the relative position. The system control unit 33 executes the second reciprocating movement upon prolonging the post-forward-movement stoppage period in the first reciprocating movement to the specified period. The system control unit 33 executes scanning on the object P in a plurality of periods during which the shift amount of the relative position is equal to or less than the predetermined threshold in the second reciprocating movement. Note that the system control unit 33 may decide an emission stoppage period in scanning executed together with the second reciprocating movement based on a slice thickness and the amplitude value of a shift amount.

Note that the system control unit 33 may reduce at least one of the velocity and acceleration of the top 22 in the forward path in the first reciprocating movement if the shift amount of the relative position exceeds the predetermined threshold in a stoppage period of the top 22 after the movement of the top 22 in the forward path in the first reciprocating movement. At this time, the system control unit 33 executes the second reciprocating movement upon reducing at least one of the velocity and acceleration of the top 22 in the forward path in the first reciprocating movement. In this case, the system control unit 33 executes scanning while executing the second reciprocating movement of the top 22.

Figure 10:
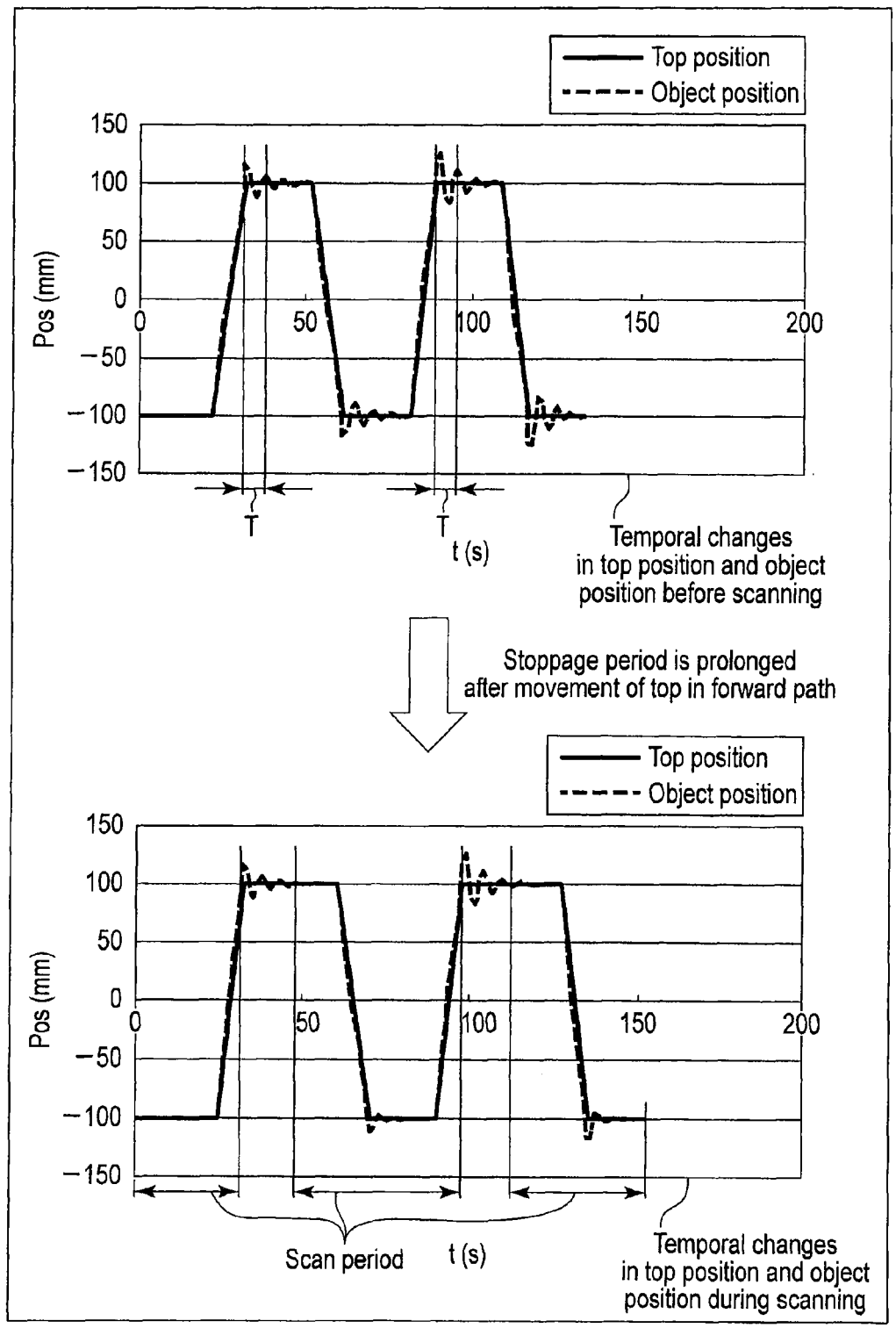
FIG. 10 is a graph showing temporal changes in the position of the top and the position of the object upon execution of the first reciprocating movement, together with temporal changes in the position of the top and the position of the object upon execution of the second reciprocating movement, according to the fourth modification of this embodiment.

FIG. 10 is a graph showing temporal changes in the position of the top and the position of the object upon execution of the first reciprocating movement, together with temporal changes in the position of the top and the position of the object upon execution of the second reciprocating movement. Referring to FIG. 10, each solid line indicates a graph representing a temporal change in the position of the top 22, and each broken line indicates a graph representing a temporal change in the position of the object P.

Referring to FIG. 10, the graphs (to be referred to as the first reciprocating movement graphs hereinafter) representing temporal changes in top position and object position before scanning are obtained by executing the first reciprocating movement. Referring to FIG. 10, the period denoted by reference symbol T is a period during which the positional shift amount exceeds the predetermined threshold.

Referring to FIG. 10, the graphs (to be referred to as the second reciprocating movement graphs hereinafter) representing temporal changes in top position and object position during scanning are those obtained by prolonging the stoppage period of the top 22 in the first reciprocating movement. As shown in FIG. 10, according to the second reciprocating movement graphs, the apparatus executes scanning on the object P in a plurality of periods during which the shift amount is equal to or less than the predetermined threshold.

According to this modification, it is possible to obtain a reconstructed image with high accuracy and reliability by suppressing the influence of the movement (vibration) of the object caused by the movement or the like of the top 22 on which the object P is placed, by executing scanning in a plurality of periods during which the shift amount is equal to or less than the predetermined threshold, in the second reciprocating movement.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray CT apparatus comprising:
    an X-ray tube configured to generate X-rays;
    an X-ray detector provided to face the X-ray tube and configured to detect the X-rays transmitted through an object;
    a data acquisition unit configured to acquire projection data of the object based on an output from the X-ray detector;
    a bed driving control unit configured to move a top to place the object along a long-axis direction of the top;
    an image processing unit configured to generate a reconstructed image based on the projection data;
    a positional shift amount detection unit configured to detect a shift amount of a position of the object relative to a position of the top, wherein the shift amount of the position of the object is due to the movement of the top along the long-axis by the bed driving control unit; and
    a positional shift processing unit configured to perform processing based on a detection result obtained by the positional shift amount detection unit.

2. The X-ray CT apparatus of claim 1, wherein the positional shift processing unit compares the shift amount of the position of the object relative to the position of the top with a predetermined threshold and, when detecting that the shift amount of the position of the object relative to the position of the top exceeds the predetermined threshold, controls the bed driving control unit to reduce at least one of a velocity and an acceleration concerning movement of the top by the bed driving control unit.

3. The X-ray CT apparatus of claim 2, further comprising a system control unit configured to decide the predetermined threshold based on at least one of an imaging condition concerning the X-rays, a slice thickness of the reconstructed image, and a diagnosis target region in the object.

4. The X-ray CT apparatus of claim 1, wherein the positional shift processing unit determines whether the shift amount of the position of the object relative to the position of the top exceeds a predetermined threshold, and notifies an operator of the X-ray CT apparatus of a determination result.

5. The X-ray CT apparatus of claim 1, wherein the positional shift processing unit compares the shift amount of the position of the object relative to the position of the top with a predetermined threshold and, when detecting that the shift amount of the position of the object relative to the position of the top exceeds the predetermined threshold, notifies the operator of the X-ray CT apparatus so as to make the operator reduce at least one of a velocity and an acceleration concerning movement of the top by the bed driving control unit.

6. The X-ray CT apparatus of claim 1, wherein the positional shift processing unit compares the shift amount of the position of the object relative to the position of the top with a predetermined threshold and, when detecting that the shift amount of the position of the object relative to the position of the top exceeds the predetermined threshold, controls the X-ray tube to delay an irradiation timing of the X-rays.

7. The X-ray CT apparatus of claim 6, further comprising a system control unit configured to decide the predetermined threshold based on at least one of an imaging condition concerning the X-rays, a slice thickness of the reconstructed image, and a diagnosis target region in the object.

8. The X-ray CT apparatus of claim 1, wherein the positional shift processing unit controls the image processing unit to perform reconstruction processing upon selecting the projection data to cancel the shift amount of the position of the object relative to the position of the top.

9. The X-ray CT apparatus of claim 1, wherein
the image processing unit generates the reconstructed image by back projection computation, and
the positional shift processing unit controls the image processing unit to perform the back projection computation upon selecting a channel and a segment on the X-ray detector in accordance with the shift amount of the position of the object relative to the position of the top to cancel the shift amount of the position of the object relative to the position of the top for each position in a target for the back projection computation.

10. An X-ray CT apparatus comprising:
an X-ray tube configured to generate X-rays;
an X-ray detector provided to face the X-ray tube and configured to detect the X-rays transmitted through an object,
a data acquisition unit configured to acquire projection data of the object based on an output from the X-ray detector;
a bed driving control unit configured to move a top to place the object along a long-axis direction of the top;
an image processing unit configured to generate a reconstructed image based on the projection data; and
a control unit configured to control the X-ray tube to generate the X-rays, when a shift amount of a position of the object relative to a position of the top becomes smaller than a predetermined threshold, wherein the shift amount of the position of the object is due to the movement of the top along the long-axis by the bed driving control unit.

11. The X-ray CT apparatus of claim 10, further comprising a system control unit configured to decide the predetermined threshold based on at least one of an imaging condition concerning the X-rays, a slice thickness of the reconstructed image, and a diagnosis target region in the object.

12. The X-ray CT apparatus of claim 1, wherein
the bed driving control unit executes first reciprocating movement to reciprocatingly move the top on which the object is placed before scanning,
the positional shift amount detection unit detects the shift amount of the position of the object relative to the position of the top in the first reciprocating movement, and
the positional shift processing unit executes second reciprocating movement to reciprocatingly move the top, together with the scanning, upon reducing at least one of a velocity and an acceleration of the top in the first reciprocating movement, when the shift amount of the position of the object relative to the position of the top exceeds the predetermined threshold.

13. The X-ray CT apparatus of claim 12, further comprising a system control unit configured to decide the predetermined threshold based on at least one of an imaging condition concerning the X-rays, a slice thickness of the reconstructed image, and a diagnosis target region in the object.

14. The X-ray CT apparatus of claim 1, wherein
the bed driving control unit executes first reciprocating movement to reciprocatingly move the top on which the object is placed before scanning,
the positional shift amount detection unit detects the shift amount of the position of the object relative to the position of the top in the first reciprocating movement, and
the positional shift processing unit
executes second reciprocating movement to reciprocatingly move the top upon prolonging a stoppage period of the top in the first reciprocating movement when the shift amount of the position of the object relative to the position of the top exceeds the predetermined threshold, and
executes the scanning in a period during which the shift amount of the position of the object relative to the position of the top is not more than the predetermined threshold in the second reciprocating movement.

15. The X-ray CT apparatus of claim 14, further comprising a system control unit configured to decide the predetermined threshold based on at least one of an imaging condition concerning the X-rays, a slice thickness of the reconstructed image, and a diagnosis target region in the object.

16. The X-ray CT apparatus of claim 14, wherein the positional shift processing unit
decides an emission stoppage period during which emission of the X-rays stops based on an amplitude of the shift amount of the position of the object relative to the position of the top and a preset slice thickness, and
stops emission of the X-rays over the emission stoppage period from a time when the shift amount of the position of the object relative to the position of the top exceeds the predetermined threshold, in the scanning executed together with the second reciprocating movement.

17. The X-ray CT apparatus of claim 16, further comprising a system control unit configured to decide the predetermined threshold based on at least one of an imaging condition concerning the X-rays, a slice thickness of the reconstructed image, and a diagnosis target region in the object.

18. The X-ray CT apparatus of claim 1, wherein
the bed driving control unit executes first reciprocating movement to reciprocatingly move the top on which the object is placed before scanning,
the positional shift amount detection unit detects the shift amount of the position of the object relative to the position of the top in the first reciprocating movement, and
the positional shift processing unit
executes second reciprocating movement to reciprocatingly move the top upon prolonging a stoppage period of the top, when the shift amount of the position of the object relative to the position of the top exceeds the predetermined threshold, in the stoppage period after movement of the top in a forward path or a backward path in the first reciprocating movement, and
executes the scanning in a plurality of periods during which the shift amount of the position of the object relative to the position of the top is not more than the predetermined threshold in the second reciprocating movement.

19. The X-ray CT apparatus of claim 18, further comprising a system control unit configured to decide the predetermined threshold based on at least one of an imaging condition concerning the X-rays, a slice thickness of the reconstructed image, and a diagnosis target region in the object.

20. The X-ray CT apparatus of claim 1, wherein
the bed driving control unit executes first reciprocating movement to reciprocatingly move the top on which the object is placed before scanning,
the positional shift amount detection unit detects the shift amount of the position of the object relative to the position of the top in the first reciprocating movement, and
the positional shift processing unit executes second reciprocating movement to reciprocatingly move the top, together with the scanning, upon reducing a velocity or an acceleration of the top in a forward path or a backward path in the first reciprocating movement which causes generation of the shift amount of the position of the object relative to the position of the top, when the shift amount of the position of the object relative to the position of the top exceeds the predetermined threshold, in a stoppage period of the top after movement of the top in the forward path or the backward path.

21. The X-ray CT apparatus of claim 20, further comprising a system control unit configured to decide the predetermined threshold based on at least one of an imaging condition concerning the X-rays, a slice thickness of the reconstructed image, and a diagnosis target region in the object.

\* \* \* \* \*